United States Patent
Izuhara

(10) Patent No.: US 7,024,710 B2
(45) Date of Patent: Apr. 11, 2006

(54) PARALLEL-LINK TABLE AND TOMOGRAPHIC IMAGING APPARATUS

(75) Inventor: Akira Izuhara, Tokyo (JP)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 69 days.

(21) Appl. No.: 10/719,074

(22) Filed: Nov. 21, 2003

(65) Prior Publication Data
US 2004/0141591 A1 Jul. 22, 2004

(30) Foreign Application Priority Data
Nov. 25, 2002 (JP) ............................. 2002-340807

(51) Int. Cl.
*A61G 7/012* (2006.01)
*A45B 9/00* (2006.01)

(52) U.S. Cl. .................. 5/601; 378/209; 108/145; 108/147; 5/611

(58) Field of Classification Search .............. 254/10 R, 254/10 C; 5/601, 611; 108/145, 147; 187/211, 187/215; 378/209
See application file for complete search history.

(56) References Cited

U.S. PATENT DOCUMENTS

| | | | |
|---|---|---|---|
| 2,922,533 A * | 1/1960 | Barge, Jr. ................ 414/746.7 |
| 3,997,926 A | 12/1976 | England | |
| 4,576,368 A * | 3/1986 | Ogawa et al. ................ 5/611 |
| 4,682,750 A * | 7/1987 | Rudolph et al. ............ 108/145 |
| 4,761,000 A | 8/1988 | Fisher et al. | |
| 5,058,871 A * | 10/1991 | Congin et al. ................ 5/610 |
| 5,131,105 A | 7/1992 | Harrawood et al. | |
| 5,205,004 A | 4/1993 | Hayes et al. | |
| 5,657,498 A * | 8/1997 | Hum ............................. 5/601 |
| 6,353,949 B1 | 3/2002 | Falbo | |
| 6,381,780 B1 | 5/2002 | Nose et al. | |
| 6,637,056 B1 * | 10/2003 | Tybinkowski et al. ......... 5/611 |

* cited by examiner

*Primary Examiner*—Michael Trettel
(74) *Attorney, Agent, or Firm*—Carl B. Horton, Esq.; Armstrong Teasdale LLP

(57) ABSTRACT

For the purpose of providing a parallel-link table that is moved up/down without moving the position of a subject in the longitudinal direction, an upper structure is placed over a base plate connected with a platform via parallel links, and a first bracket on the upper structure and a middle point of one parallel link are connected by a first position correcting link of a length half that of the parallel link using pivotal joint portions; and therefore, when the base plate is moved up/down with respect to the platform, the upper structure moves only in the vertical direction without moving in the horizontal direction, and the top plate over the upper structure, hence, the subject placed on the top plate can be moved up/down in the vertical direction without moving in the longitudinal direction.

19 Claims, 6 Drawing Sheets

PARALLEL-LINK TABLE AND TOMOGRAPHIC IMAGING APPARATUS

CROSS REFERENCE TO RELATED APPLICATIONS

This application claims the benefit of Japanese Application No. 2002-340807 filed Nov. 25, 2002.

BACKGROUND OF THE INVENTION

The present invention relates to a parallel-link table for supporting a subject and carrying the subject to an imaging region and a tomographic imaging apparatus.

In recent years, a table having an elevation mechanism of a parallel-link type is used in positioning a subject that horizontally lies in an imaging region of a tomographic imaging apparatus (see, for example, Patent Document 1). Since the table can be configured to have a smaller area occupied by the elevation mechanism portion, its appearance can be made very elegant, and the elevation mechanism portion can be manufactured at a relatively low cost.

[Patent Document 1]

Japanese Patent Application Publication No. H02-036098 (page 3, FIG. 2).

According to the conventional technique as described above, however, a top plate for supporting the subject moves in a longitudinal direction while moving up/down. Specifically, an upper structure or a base plate on which the top plate is placed is coupled to a platform over which these members are mounted via parallel links, and therefore, the top plate must move in the longitudinal direction as it moves up/down.

Especially when the subject is moved between a stretcher and tables a work position away from an image acquisition section of the tomographic imaging apparatus is preferable from the viewpoint of operation ease. However, the position of the top table is close to the image acquisition section when the conventional parallel-link table is fixed at a height approximately the same as the stretcher, which has been a cause of poor operation ease.

Thus, it is important to find a way to realize a parallel-link table and tomographic imaging apparatus in which the table is moved up/down without moving the position of the subject in the longitudinal direction.

SUMMARY OF THE INVENTION

Therefore, an object of the present invention is to provide a parallel-link table and tomographic imaging apparatus in which the table is moved up/down without moving the position of the subject in the longitudinal direction.

In order to solve the aforementioned problem and attain the object, a parallel-link table, in accordance with a first aspect of the invention, is characterized in comprising: a top plate for supporting a subject; an upper structure for supporting said top plate, said upper structure moving relative to said top plate only in a longitudinal direction of said top plate; a base plate for supporting said upper structure, said base plate moving relative to said upper structure only in said longitudinal direction; a platform on a floor, for supporting said top plate, said upper structure and said base plate; a first bracket of a height greater than a distance between said upper structure and said base plate, said first bracket being secured to said upper structure on a side near said platform; parallel links for coupling said base plate and said platform using movable joint portions; a first position correcting link of a length half that of said parallel links, for connecting a middle point of one of said parallel links and said first bracket portion lying on said base plate in said longitudinal direction by movable joint portions; and a first actuator portion for moving said upper structure up/down with respect to said platform.

In the invention of the first aspect, a top plate supports a subject, an upper structure supports the top plate and moves relative to the top plate only in a longitudinal direction of the top plate, a base plate supports the upper structure and moves relative to the upper structure only in the longitudinal direction, a platform on a floor supports the top plate, upper structure and base plate, a first bracket of a height greater than a distance between the upper structure and base plate is secured to the upper structure on a side near the platform, parallel links couple the base plate and the platform using movable joint portions, a first position correcting link of a length half that of the parallel links connects a middle point of one of the parallel links and the first bracket portion lying on the base plate in the longitudinal direction by movable joint portions, and a first actuator portion moves the upper structure up/down with respect to the platform; and therefore, when the upper structure is moved up/down with respect to the platform, the upper structure, hence, the position of the subject lying on the upper structure, can be moved up/down in the vertical direction without moving in the longitudinal direction, and an operator can work at a position away from the image acquisition section in moving the subject from/to a stretcher with the top plate moved up, thereby improving work efficiency for the operator.

The parallel-link table, in accordance with a second aspect of the invention, is characterized in that: said upper structure has said first bracket in a portion between said parallel links.

In the invention of the second aspect, since the upper structure has the first bracket in a portion between the parallel links, an area occupied by a mechanical portion associated with the up/down movement can be reduced.

A parallel-link table, in accordance with a third aspect of the invention, is characterized in comprising: a top plate for supporting a subject; an upper structure for supporting said top plate, said upper structure moving relative to said top plate only in a longitudinal direction of said top plate, a base plate for supporting said upper structure, said base plate moving relative to said upper structure only in said longitudinal direction; a second bracket of a height greater than a distance between said upper structure and said base plate, said second bracket being secured to said upper structure on a side near a platform; a platform on a floor, for supporting said top plate, said upper structure, said base plate and said second bracket; parallel links for coupling said base plate and said platform using movable joint portions; a third bracket lying in a plane between said joint portions on said base plate, said third bracket being movable relative to said base plate only in said longitudinal direction; a second position correcting link for connecting a middle point of one of said parallel links and said third bracket, said second position correcting link having a length half that of said link; a second actuator portion connecting said third and second brackets; and a first actuator portion for moving said upper structure up/down with respect to said platform.

In the invention of the third aspect, a top plate supports a subject, an upper structure supports the top plate and moves relative to the top plate only in a longitudinal direction of the top plate, a base plate supports the upper structure and moves relative to the upper structure only in the longitudinal direction, a second bracket of a height greater than a distance between the upper structure and base plate is secured to the upper structure on a side near a platform, a platform on a floor supports the top plate, upper structure, base plate and second bracket, parallel links couple the base plate and the platform using movable joint portions, a third bracket lying in a plane between the joint portions on the base plate moves relative to the base plate only in the longitudinal direction, a second position correcting link of a length half that of one of the parallel links connects a middle point of the link and the third-bracket, a second actuator portion connects the third and second brackets, and a first actuator portion moves the upper structure up/down with respect to the platform; and therefore, when the upper structure is moved up/down with respect to the platform, the third bracket moves up/down only in the vertical direction without moving in the longitudinal direction, whereby the upper structure can be controlled to move in the longitudinal direction with reference to the third bracket and the position of the subject lying on the top plate can be accurately known, and hence, a driving portion for moving the top plate in the longitudinal direction can be reduced in size and cost.

The parallel-link table, in accordance with a fourth aspect of the invention, is characterized in that: said joint portions on said base plate or on said platform lie at a distance greater than half that of said link.

In the invention of the fourth aspect, since the joint portions on the base plate or on the platform lie at a distance greater than half that of the link, the table can be moved down to a level at which the base plate and platform come close to each other.

The parallel-link table, in accordance with a fifth aspect of the invention, is characterized in that: said base plate and said third bracket are connected by a linear guide.

In the invention of the fifth aspect, since the base plate and third bracket are connected by a linear guide, they can be moved relative to each other smoothly and only in the longitudinal direction.

The parallel-link table, in accordance with a sixth aspect of the invention, is characterized in that: said first and second actuator portions comprise a chain-belt driving portion or a roller frictional driving portion.

In the invention of the sixth aspect, since the first and second actuator portions comprise a chain-belt driving portion or a roller frictional driving portion, the links etc. can be moved by the chain-belt or roller.

The parallel-link table, in accordance with a seventh aspect of the invention, is characterized in that: said first and second actuator portions comprise a cylinder having an extendable piston rod.

In the invention of the seventh aspect, since the first and second actuator portions are extended/contracted by a cylinder having a piston rod, the links etc. can be moved by the extendable piston rod.

The parallel-link table, in accordance with an eighth aspect of the invention, is characterized in that: said cylinder is connected between said platform and said link using movable joint portions.

In the invention of the eighth aspect, since the cylinder is connected between the platform and link using movable joint portions, the upper structure can be easily and efficiently moved.

The parallel-link table, in accordance with a ninth aspect of the invention, is characterized in that: said platform has the joint portion with said cylinder in a portion between the joint portions of said parallel links.

In the invention of the ninth aspect, since the platform has the joint portion with the cylinder in a portion between the joint portions of the parallel links, a mechanical portion for moving up/down the upper structure can be made compact by accommodating the mechanism section within the parallel links.

The parallel-link table, in accordance with a tenth aspect of the invention, is characterized in that: said upper structure and said base plate are connected by a linear guide.

In the invention of the tenth aspect, since the upper structure and base plate are connected by a linear guide, they can be moved relative to each other smoothly and only in the longitudinal direction.

The parallel-link table, in accordance with an eleventh aspect of the invention, is characterized in that said cylinder extends/contracts the piston rod by hydraulic control.

In the invention of the eleventh aspect, since the cylinder extends/contracts the piston rod by hydraulic control; a heavy object can be smoothly moved.

The parallel-link table, in accordance with a twelfth aspect of the invention, is characterized in that: said cylinder extends/contracts the piston rod by motor control.

In the invention of the twelfth aspect, since the cylinder extends/contracts the piston rod by motor control, extension/contraction can be controlled with high accuracy.

The parallel-link table, in accordance with a thirteenth aspect of the invention, is characterized in that: said parallel links are covered with a plate material.

In the invention of the thirteenth aspect, since the parallel links are covered with a plate material, a mechanical portion for moving up/down the upper structure can be covered with a low-cost material, and the table can be made in a design with sleek appearance.

The parallel-link table, in accordance with a fourteenth aspect of the invention, is characterized in that: said upper structure comprises a driving portion for moving said top plate in the longitudinal direction.

In the invention of the fourteenth aspect, since the upper structure moves the top plate in the longitudinal direction by a driving portion, the position of the subject can be automatically moved to a specified position.

A tomographic imaging apparatus, in accordance with a fifteenth aspect of the invention, comprises: a table section for carrying a subject placed thereon to an imaging region; an image acquisition section for acquiring tomographic image information from said subject lying in said imaging region; and a control section for controlling the carrying of said subject to said imaging region and the acquisition of said tomographic image information, and is characterized in that: said table section comprises: a top plate for supporting said subject in a horizontally lying position; an upper structure for supporting said top plate, said upper structure being movable relative to said top plate only in a longitudinal direction of said top plate; a base plate for supporting said upper structure, said base plate being movable relative to said upper structure only in said longitudinal direction; a platform on a floor, for supporting said top plate, said upper structure and said base plate; a first bracket of a height greater than a distance between said upper structure and said base plate, said first bracket being secured to said upper structure on a side near said platform; parallel links for coupling said base plate and said platform using movable joint portions; a first position correcting link of a length half that of said parallel links, for connecting a middle point of one of said parallel links and said first bracket portion lying on said base plate in said longitudinal direction by movable joint portions; and a first actuator portion for moving said upper structure up/down with respect to said platform.

In the invention of the fifteenth aspect, in the table section, a top plate supports a subject, an upper structure that is movable relative to the top plate only in a longitudinal direction of the top plate supports the top plate, a base plate that is movable relative to the upper structure in the longitudinal direction supports the upper structure, a platform on a floor supports the top plate, upper structure and base plate, a first bracket of a height greater than a distance between the upper structure and base plate is secured to the upper structure on a side near the platform, parallel links couple the base plate and the platform using movable joint portions, a first position correcting link of a length half that of one of the parallel links connects a middle point of the link and the first bracket portion lying on the base plate in the longitudinal direction by movable joint portions, and a first actuator portion moves the upper structure up/down with respect to the platform; and therefore, when the upper structure is moved up/down with respect to the platform, the upper structure, hence, the position of the subject lying on the upper structure, can be moved up/down in the vertical direction without moving in the longitudinal direction, and an operator can work at a position away from the image acquisition section in moving the subject from/to a stretcher with the top plate moved up, thereby improving work, efficiency for the operator.

A tomographic imaging apparatus, in accordance with a sixteenth aspect of the invention, comprises: a table section for carrying a subject placed thereon to an imaging region; an image acquisition section for acquiring tomographic image information from said subject lying in said imaging region; and a control section for controlling the carrying of said subject to said imaging region and the acquisition of said tomographic image information, and is characterized in that: said table section comprises: a top plate for supporting said subject in a horizontally lying position; an upper structure for supporting said top plate, said upper structure being movable relative to said top plate only in a longitudinal direction of said top plate; a base plate for supporting said upper structure, said base plate being movable relative to said upper structure only in said longitudinal direction; a second bracket of a height greater than a distance between said upper structure and said base plate, said second bracket being secured to said upper structure on a side near a platform; a platform on a floor, for supporting said top plate, said upper structure, said base plate and said second bracket; parallel links for coupling said base plate and said platform using movable joint portions; a third bracket lying in a plane between said joint portions on said base plate, said third bracket being movable relative to said base plate only in said longitudinal direction; a second position correcting link for connecting a middle point of one of said parallel links and said third bracket, said second position correcting link having a length half that of said link; a second actuator portion for connecting said third and second brackets; and a first actuator portion for moving said upper structure up/down with respect to said platform.

In the invention of the sixteenth aspect, in the table section, a top plate supports a subject, an upper structure that is movable relative to the top plate only in a longitudinal direction of the top plate supports the top plate, a base plate that is movable relative to the upper structure in the longitudinal direction supports the upper structure, a second bracket of a height greater than a distance between the upper structure and base plate is secured to the upper structure on a side near a platform, a platform on a floor supports the top plate, upper structure, base plate and second bracket, parallel links couple the base plate and the platform using movable joint portions, a third bracket that is movable relative to the base plate only in the longitudinal direction is placed in a plane between the joint portions on the base plate, a second position correcting link of a length half that of one of the parallel links connects a middle point of the link and third bracket, a second actuator portion connects the third and second brackets, and a first actuator portion moves the upper structure up/down with respect to the platform; and therefore, when the upper structure is moved up/down with respect to the platform, the third bracket moves up/down only in the vertical direction without moving in the longitudinal direction, whereby the upper structure can be controlled to move in the longitudinal direction with reference to the third bracket and the position of the subject lying on the top plate can be accurately known, and hence, a driving section for moving the top plate in the longitudinal direction can be reduced in size and cost.

The tomographic imaging apparatus, in accordance with a seventeenth aspect of the invention, is characterized in that: said first and second actuator portions comprise a chain-belt driving portion or a roller frictional driving portion.

In the invention of the seventeenth aspect, since the first and second actuator portions comprise a chain-belt driving portion or a roller frictional driving portion, the links etc. can be moved by the chain-belt or roller.

The tomographic imaging apparatus, in accordance with an eighteenth aspect of the invention, is characterized in that: said first and second actuator portions comprise a cylinder having an extendable piston rod.

In the invention of the eighteenth aspect, since the first and second actuator portions are extended/contracted by a cylinder having a piston rod, the links etc. can be moved by the extendable piston rod.

According to the present invention, a top plate supports a subject, an upper structure supports the top plate and is movable relative to the top plate only in a longitudinal direction of the top plate, a base plate supports the upper structure and is movable relative to the upper structure in the longitudinal direction, a platform on a floor supports the top plate, upper structure and base plate, a first bracket secured to the upper structure on a side near the platform has a height greater than a distance between the upper structure and the base plate, parallel links couple the base plate and the platform using movable joint portions, a first position correcting link of a length half that of the parallel links connects a middle point of one of the parallel links and the first bracket portion lying on the base plate in the longitudinal direction by movable joints, and a first actuator portion moves the upper structure up/down with respect to the platform; and therefore, when the upper structure is moved up/down with respect to the platform, the upper structure, hence, the position of the subject lying on the upper structure, can be moved up/down in the vertical direction without moving in the longitudinal direction, and an operator can work at a position away from the image acquisition section in moving the subject from/to a stretcher with the top plate moved up, thereby improving work efficiency for the operator.

Further objects and advantages of the present invention will be apparent from the following description of the preferred embodiments of the invention as illustrated in the accompanying drawings.

DETAILED DESCRIPTION OF THE INVENTION

Preferred embodiments of a parallel-link table and a tomographic imaging apparatus in accordance with the present invention will now be described with reference to accompanying drawings.

(Embodiment 1)

Figure 1:
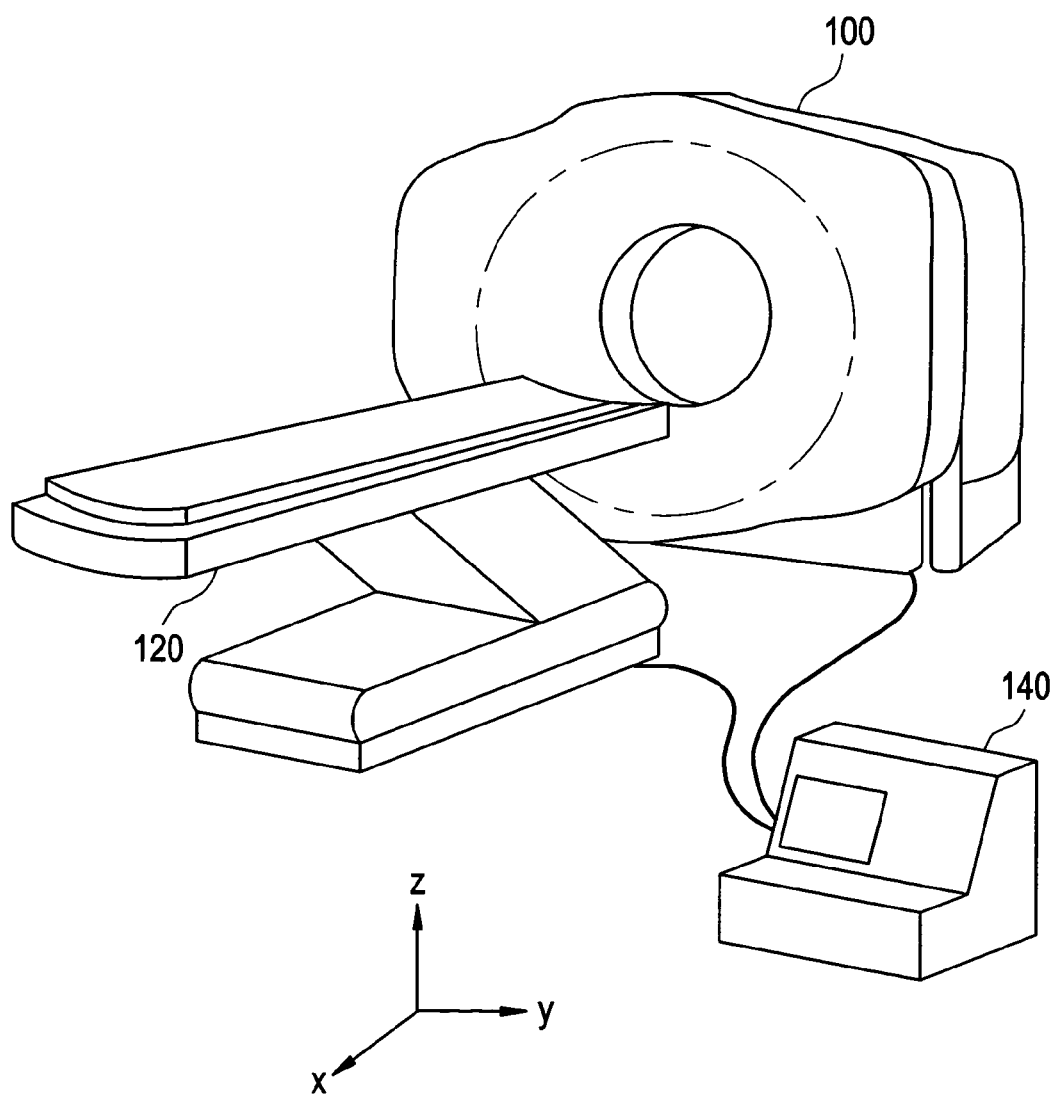
FIG. 1 is a general external view showing the overall configuration of a tomographic imaging apparatus.

An overall configuration of a tomographic imaging apparatus using an X-ray CT apparatus in accordance with Embodiment 1 will be first described. FIG. 1 shows a general external view of the X-ray CT apparatus. As shown in FIG. 1, the present apparatus comprises an X-ray transmission data acquisition section 100, which is an image acquisition section, a table section 120, and an operation console section 140.

The table section 120 comprises an up/down moving mechanism and a top plate. The up/down moving mechanism adjusts the height of the top plate. A subject is laid on the top plate, and is moved along with the top plate by means that is not shown to a position most suitable for imaging.

The X-ray transmission data acquisition section 100 conducts imaging on the subject, and acquires X-ray transmission data. The operation console section 140 controls the X-ray transmission data acquisition section 100 and table section 120 based on information input by an operator, and acquires an optimum tomographic image of the subject.

Figure 2:
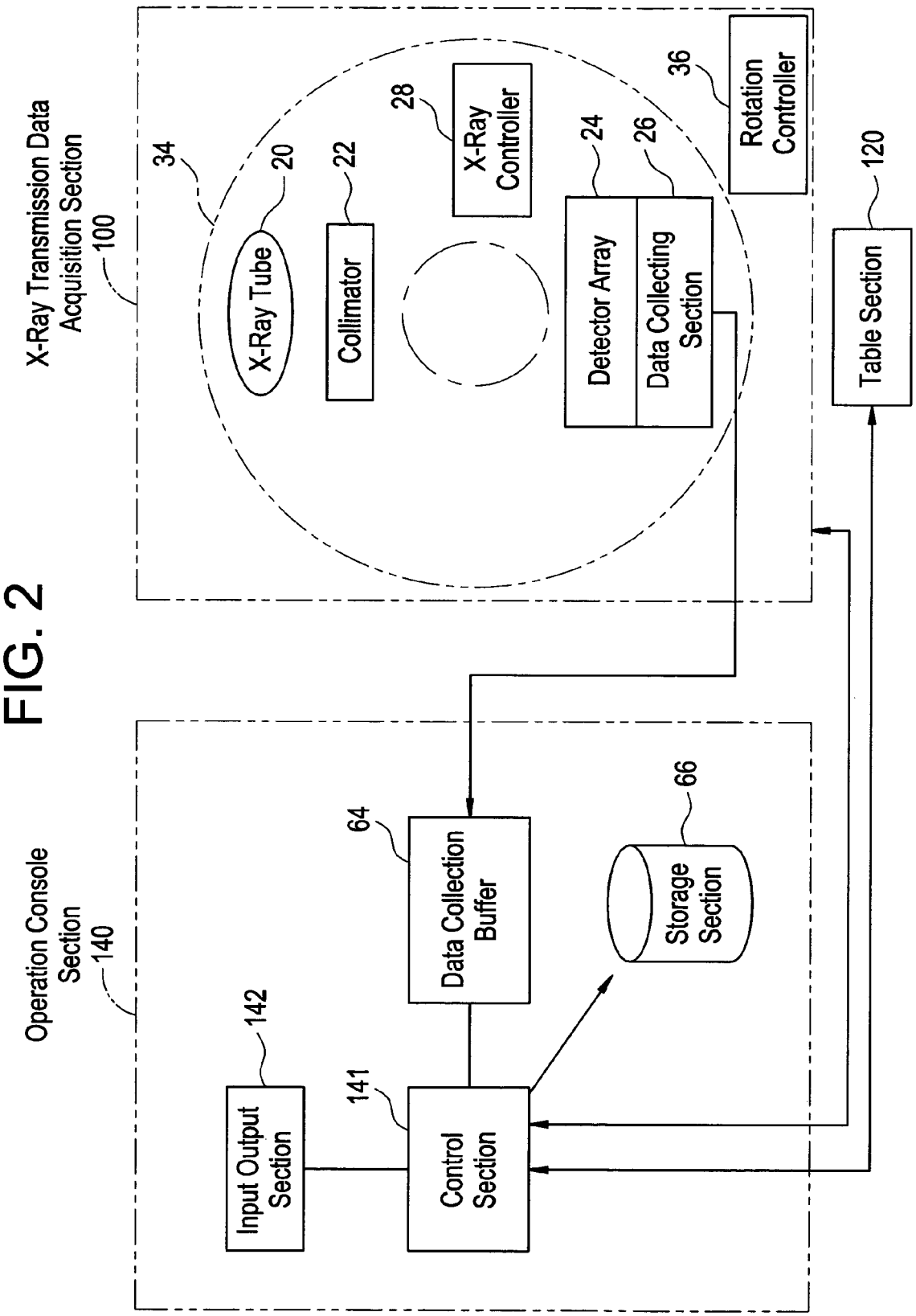
FIG. 2 is a block diagram showing the tomographic imaging apparatus of Embodiment 1.

FIG. 2 is a block diagram showing the overall configuration of the X-ray CT apparatus. The X-ray transmission data acquisition section 100 comprises an X-ray tube 20, a collimator 22 and an X-ray detector 24, which together constitute an X-ray emitting/detecting apparatus. X-rays emitted from the X-ray tube 20 are shaped by the collimator 22 into, for example, a fan-shaped X-ray beam, i.e., fan-beam X-rays, and are directed to the X-ray detector 24.

The X-ray detector 24 has a plurality of X-ray detecting elements arranged in an array in an extending direction of the fan-beam X-rays. The X-ray detector 24 is a multi-channel X-ray detector in which the plurality of X-ray detecting elements are arranged in an array.

The X-ray detector 24 is connected with a data collecting section 26. The data collecting section 26 collects data detected by the individual X-ray detecting elements in the detector array. Emission of X-rays from the X-ray tube 20 is controlled by an X-ray controller 28 in the X-ray transmission data acquisition section 100.

The X-ray tube 20 through X-ray controller 28 are mounted on a rotating section 34 of the X-ray transmission data acquisition section 100. The subject is rested on the top plate placed in a bore in the center of the rotating section 34 in a horizontally lying position. The rotating section 34 is controlled to rotate by a rotation controller 36, emits X-rays from the X-ray tube 20, and detects transmitted X-rays from the subject at the detector array.

The operating console section 140 comprises a control section 141, a data collection buffer 64, an input/output section 142, and a storage section 66. The control section 141 is connected with the data collection buffer 64, which is in turn connected to the data collecting section 26 in the X-ray transmission data acquisition section 100. Data collected at the data collecting section 26 are input to the control section 141 via the data collection buffer 64.

The control section 141 conducts image reconstruction using transmission X-ray signals, i.e., projection data, collected via the data collection buffer 64. The control section 141 is also connected with the storage section 66. The storage section 66 stores the projection data collected in the data collection buffer 64, reconstructed tomographic image information, programs for implementing the function of the present apparatus, and the like.

The control section 141 is also connected with the input/output section 142. The input/output section 142 has a display device and an operation device, and displays the tomographic image information output by the control section 141 and other information. The input/output section 142 is operated by the operator, and supplies several kinds of instructions and information to the control section 141 from the operation device. The operator interactively operates the present apparatus using the display device.

Moreover, the control section 141 is connected with the table section 120, and conducts height control for an elevating section in the table section 120 and position control for the top plate in the elevating section, for example. The subject on the top plate is thus positioned at a position most suitable for image acquisition.

Figure 3:
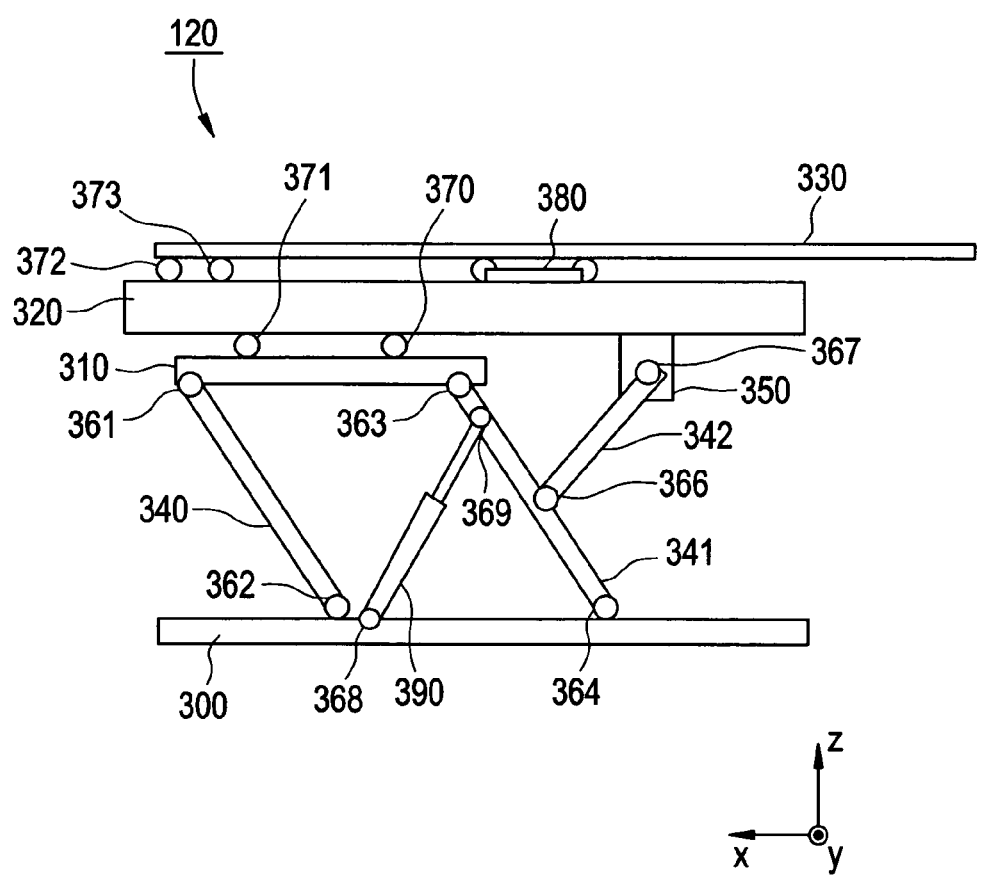
FIG. 3 shows a table section of Embodiment 1.

FIG. 3 is a side view showing a mechanical portion of the table section 120. The table section 120 comprises a top plate 330, an upper structure 320, a base plate 310, and a platform 300. The subject is placed on the top plate 330. The top plate 330 is mounted on the upper structure 320, and the top plate 330 and upper structure 320 are connected by slide portions 372 and 373 and a driving portion 380. The platform 300 is installed on a floor, and supports the top plate 330, upper structure 320, base plate 310 and the like.

The top plate 330 is capable of moving relative to the upper structure 320 only in the longitudinal direction by the slide portions 372 and 373. While the slide portions 372 and 373 are schematically shown in FIG. 3, a linear guide, for example, may be used to allow the top plate 330 to move relative to the upper structure 320 smoothly and only in the longitudinal direction. Moreover, the top plate 330 is controlled in position and is moved in the longitudinal direction by the driving portion 380. The driving portion 380 is connected with and controlled by the control section 141 in the operation console section 140 via wiring that is not shown.

The upper structure 320 is mounted on the base plate 310 and connected therewith by slide portions 370 and 371. The slide portions 370 and 371 allow the upper structure 320 and base plate 310 to move relative to each other only in the longitudinal direction, similarly to the slide portions 372 and 373.

The upper structure 320 also comprises a first bracket 350. The first bracket 350 is secured to the upper structure 320 on a side near the platform 300, and has a protruding portion protruding to a level approximately the same as the height of the base plate 310.

The platform 300 is installed on the floor, and supports the top plate 330, upper structure 320, base plate 310 and the like. The platform 300 and base plate 310 are connected by parallel links 340 and 341 of equal lengths. The parallel links 340 and 341 are coupled to the platform 300 and the base plate 310 via joint portions 361–364. The joint portions 361–364 form pivotal joints, and joined portions are freely rotatable altogether in an x-z plane of FIG. 3 around the joint portions. Thus, the base plate 310, platform 300 and parallel links 340 and 341 form a parallelepiped parallel crank, and the base plate 310 and platform 300 move up/down while maintaining their parallel relationship.

A first actuator portion 390 is connected between one parallel link 341 and the platform 300. The first actuator portion 390 is comprised of a cylinder incorporating therein a piston rod, which is extended/contracted by hydraulic pressure, for example. The ends of the first actuator portion 390 are connected to the platform 300 and the parallel link 341 by joint portions 368 and 369. The joint portions 368 and 369 form pivotal joints, and joined portions are freely rotatable altogether in the x-z plane of FIG. 3 around the joint portions. The extension/contraction of the piston rod causes the base plate 310 to move up/down with respect to the platform 300. The first actuator portion 390 is connected with and controlled by the control section 141 in the operation console section 140 via wiring that is not shown.

A middle point of the parallel link 341 between the joint portions 363 and 364 and a portion of the first bracket 350 that is approximately level with the height of the base plate 310 from the platform 300 are connected by a first position correcting link 342. The first position correcting link 342 is coupled with the parallel link 341 and first bracket by joint portions 366 and 367. The joint portions 366 and 367 form pivotal joints, and joined portions are freely rotatable altogether in the x-z plane of FIG. 3 around the joint portions.

Figure 4A:
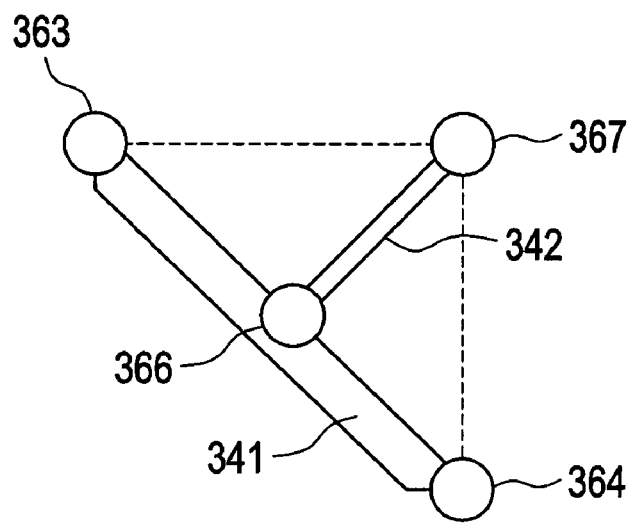
FIG. 4 shows the operation of a mechanical portion of the table section of Embodiment 1.

The operation of up/down movement of the table section 120 will now be described with reference to FIG. 4. FIG. 4(A) shows a mechanical portion around the first position correcting link 342 in the table section 120.

The joint portion 366 at the middle point of the parallel link 341 is connected to the joint portion 367 by the first position correcting link 342 of a length half that of the parallel link 341. The joint portions 363 and 367 are maintained at a generally horizontal position by the base plate 310 and the first bracket 350 on the upper structure 320. Under such conditions, a triangle formed by the joint portions 363, 364 and 367 is geometrically certain of always forming a right angle at the joint portion 367.

Figure 4B:
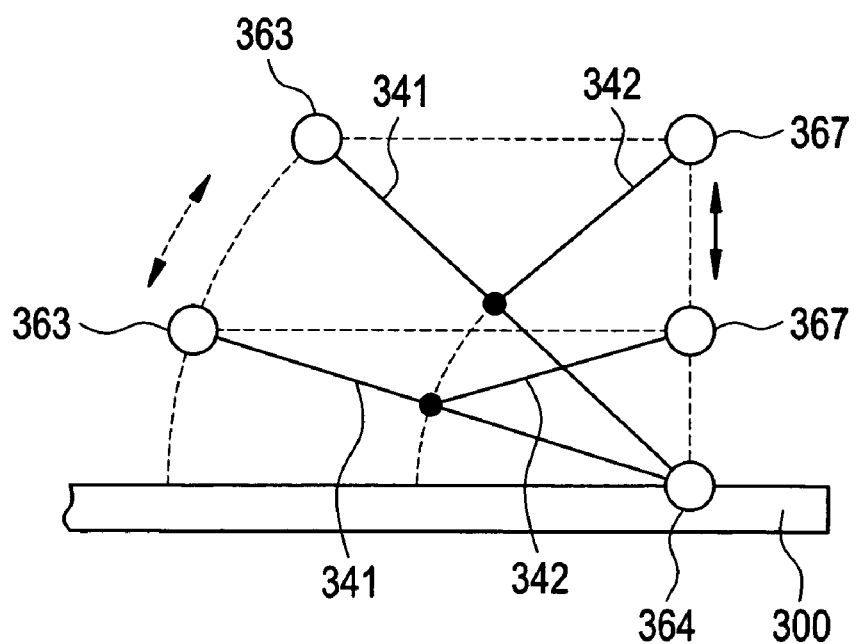

FIG. 4(B) exemplarily shows an operation of the mechanical portion shown in FIG. 4(A) while the table section 120 moves up/down. The parallel link 341 is subject to a push or pull force from the platform 300 by extension/contraction of the first actuator portion 390.

This causes the joint portion 363 on the parallel link 341 to move in the vertical direction while circularly moving around the joint portion 364 that is another end of the parallel link 341 secured to the platform 300. At that time, the base plate 310 to which the joint portion 363 is secured moves similarly to the joint portion 363.

On the other hand, the position of the joint portion 367 is always maintained in a horizontal direction with respect to the joint portion 363 because the upper structure 320 and base plate 310 are capable of freely moving only in the longitudinal direction, i.e., in the horizontal direction. When the joint portion 363 moves down such as in the operation shown in FIG. 4(B), for example, the triangle formed by the joint portions 363, 364 and 367 deforms while maintaining the right angle at the joint portion 367.

Accordingly, the joint portion 367 moves up/down only in the vertical direction without moving in the horizontal direction. As a result, the upper structure 320 to which the joint portion 367 is secured also moves up/down only in the vertical direction without moving in the horizontal direction. At that time, the base plate 310 to which the joint portion 363 is secured and the upper structure 320 to which the joint portion 367 is secured slide in the horizontal direction to lie at a horizontal distance away from each other.

Moreover, the top plate 330 over the upper structure 320, and hence, the subject supported on the top plate 330, move up/down only in the vertical direction without moving in the horizontal direction, along with the upper structure 320.

As described above, in Embodiment 1, the upper structure 320 is placed over the base plate 310 connected with the platform 300 via the parallel links 340 and 341, and the first bracket 350 on the upper structure 320 and the middle point of the parallel link 341 are connected by the first position correcting link 342 of a length half that of the parallel link 341 using the pivotal joint portions 366 and 367; and therefore, when the base plate 310 is moved up/down with respect to the platform 300, the upper structure 320 moves only in the vertical direction without moving in the horizontal direction, and the top plate 330 over the upper structure 320, hence, the subject placed on the top plate 330, can be moved up/down in the vertical direction without moving in the longitudinal direction.

Moreover, although an X-ray CT apparatus is employed as the tomographic imaging apparatus in Embodiment 1, the present invention is not limited thereto and may be applied to a magnetic resonance imaging apparatus, a gamma camera, a positron CT, or the like.

Furthermore, although a cylinder having a piston rod is employed for the first actuator portion 390 in Embodiment 1, other driving means, such as a chain-belt drive or roller frictional drive may be used.

(Embodiment 2)

While the first bracket 350 is disposed outside the parallel links 340 and 341 in Embodiment 1, it may be disposed within the parallel links 340 and 341 close to the base plate 310. Embodiment 2 will therefore show a case in which the first bracket is disposed within the parallel links 340 and 341.

Figure 5:
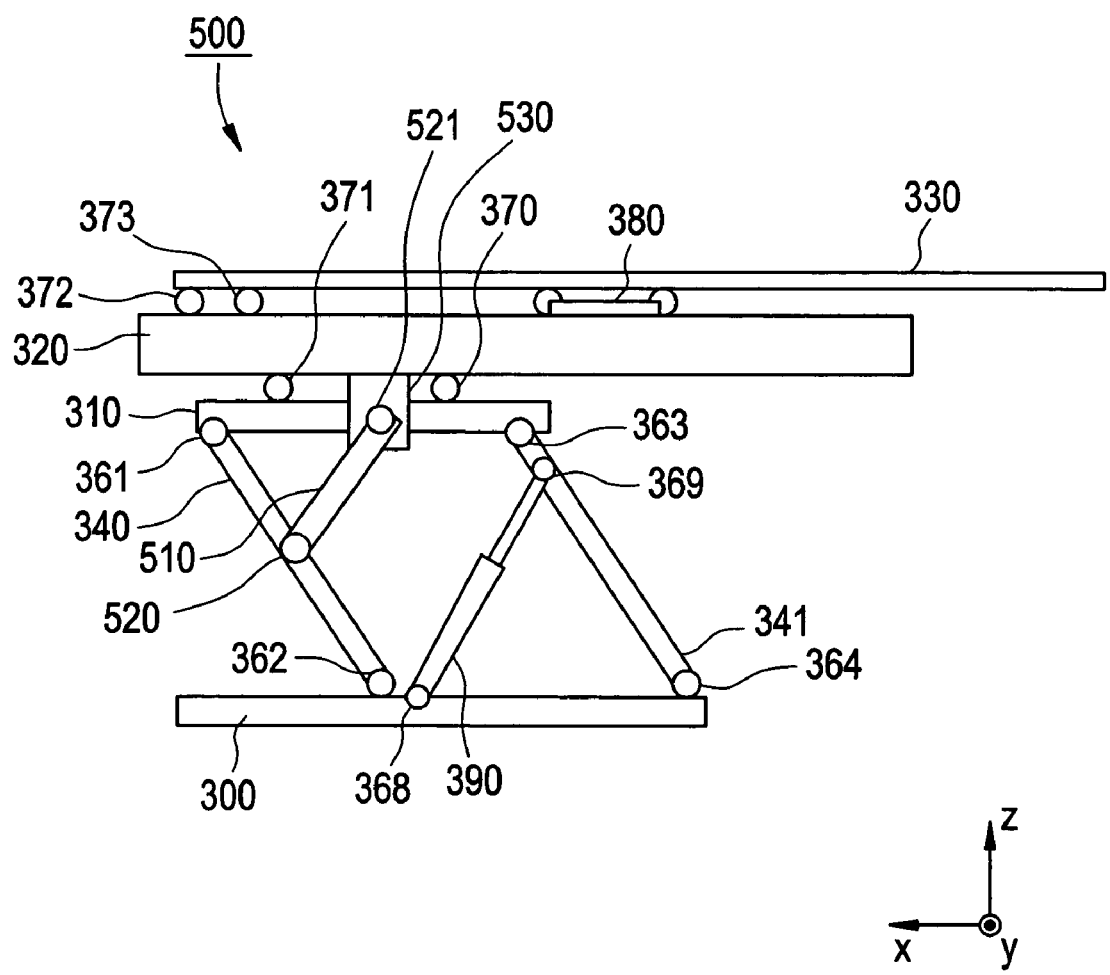
FIG. 5 shows a table section of Embodiment 2.

FIG. 5 is a side view showing a mechanical portion of a table section 500 in accordance with Embodiment 2. Since the table section 500 corresponds to the table section 120 shown in FIG. 1, and the remainder of the configuration is similar to that shown in FIGS. 1 and 2, detailed description thereof will be omitted here.

Moreover, since the table section 500 is similar to the table section 120 shown in FIG. 3 except for the positions of the first bracket 350 secured to the upper structure 320 and of the first position correcting link 324, detailed description of the remainder of the configuration will be omitted.

The upper structure 320 has a first bracket 530 in a region between the joint portions 361 and 362 on the base plate 310. The first bracket 530 is secured to the upper structure 320 on a side near the platform 300, and has a protruding portion protruding to a level the same as the height of the base plate 310. Moreover, the protruding portion of the first bracket 530 and the base plate 310 have a mechanism (not shown) that enables them to move in the horizontal direction with respect to each other.

A middle point of the parallel link 340 between the joint portions 361 and 362 and the protruding portion of the first bracket 530 level with the base plate 310 are connected by a second position correcting link 510. The second position correcting link 510 is coupled to the parallel link 340 and the first bracket 530 by joint portions 520 and 521. The joint portions 520 and 521 form pivotal joints, and joined portions are freely rotatable altogether in an x-z plane of FIG. 5 around the joint portions.

The operation of the parallel link 340 and second position correcting link 510 is exactly the same as the operation of the parallel link 341 and first position correcting link 342 shown in FIG. 4, and description thereof will be omitted.

As described above, in Embodiment 2, the first bracket 530 on the upper structure 320 is disposed in a region between the joint portions 361 and 363 on the base plate 310, and is connected with the middle point of the parallel link 340 by the second position correcting link 510; and therefore, the first bracket 530 and the second position correcting link 510 are confined in the region between the parallel links 340 and 341, and the area occupied by the mechanical portion associated with the up/down movement of the top plate 330 is reduced, thereby giving the table section 500 an elegant appearance.

(Embodiment 3)

While the upper structure 320 moves up/down only in the vertical direction in Embodiment 2, it may be moved in the horizontal direction independent of the up/down movement. Embodiment 3 will therefore show a case in which the upper structure 320 moves in the horizontal direction with respect to the base plate 310 independent of up/down movement.

Figure 6:
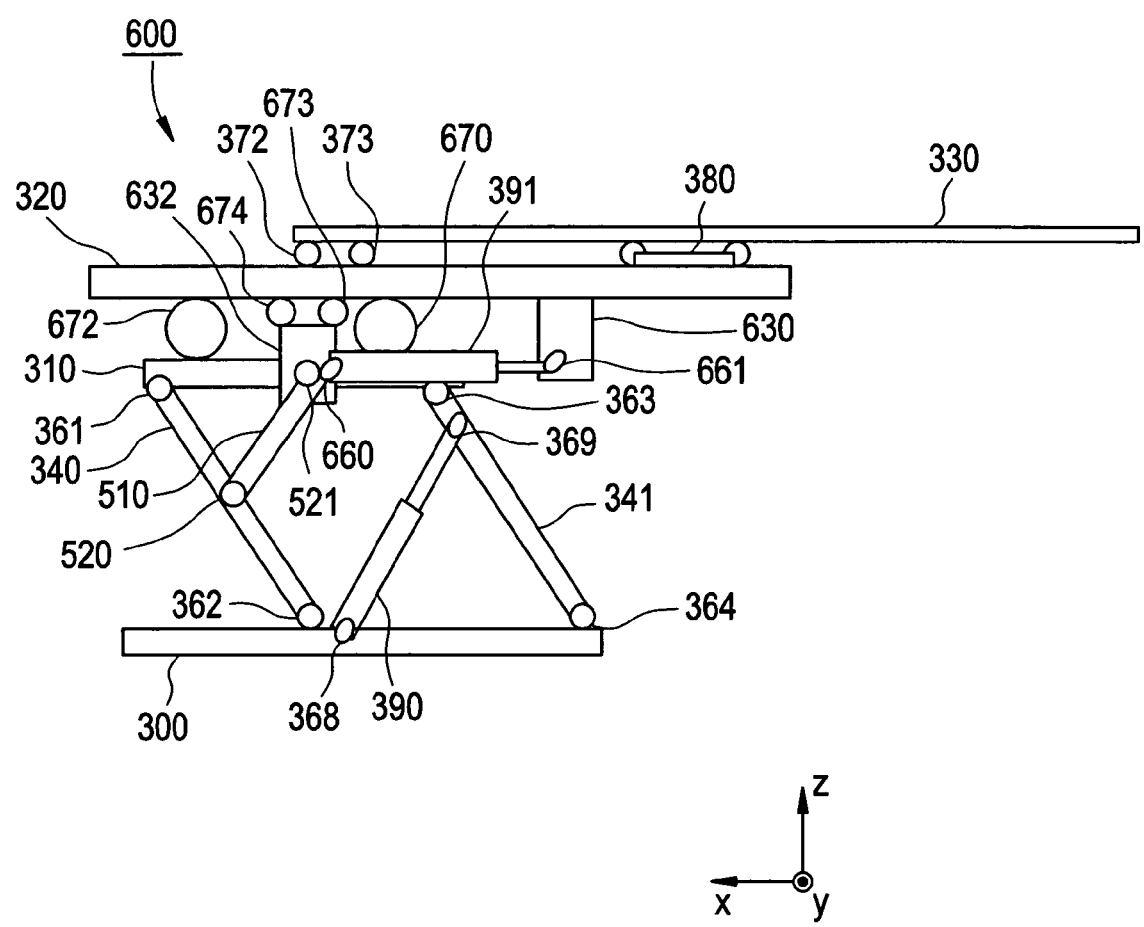
FIG. 6 shows a table section of Embodiment 3.

FIG. 6 is a side view showing a mechanical portion of a table section 600 in accordance with Embodiment 3. Since the table section 600 corresponds to the table section 120 shown in FIG. 1, and the remainder of the configuration is similar to that shown in FIGS. 1 and 2, detailed description thereof will be omitted here.

Moreover, since the table section 600 is different from the table section 500 shown in FIG. 5 in the upper structure 320 and the first bracket 530 secured to the upper structure 320, description will be focused on this portion and description on the remainder of the configuration will be omitted.

The base plate 310 of the table section 600 has a third bracket 632 in a region between the joint portions 361 and 363. The base plate 310 is connected with the upper structure 320 by slide portions 670 and 672 and is movable relative to the upper structure 320 only in the horizontal direction; at the same time, the third bracket 632 is also connected with the upper structure 320 by slide portions 673 and 674 and is movable relative to the upper structure 320 only in the horizontal direction. The third bracket 632 and base plate 310 have a mechanism (not shown) that enables them to move in the horizontal direction with respect to each other.

A middle point of the parallel link 340 between the joint portions 361 and 362 and the third bracket 632 are connected by the second position correcting link 510. The second position correcting link 510 is coupled to the parallel link 340 and the third bracket 632 by the joint portions 520 and 521. The joint portions 520 and 521 form pivotal joints, and joined portions are freely rotatable altogether in an x-z plane of FIG. 6 around the joint portions.

The upper structure 320 has a second bracket 630. The second bracket 630 is secured to the upper structure 320 away from the base plate 310 on a side near the platform 300, and has a protruding portion protruding to a level approximately the same as the height of the base plate 310.

The second and third brackets 630 and 632 are connected by a second actuator portion 391. The second actuator portion 391 is comprised of a cylinder incorporating therein a piston rod, which is extended/contracted by hydraulic pressure, for example. The ends of the second actuator portion 391 are connected to the third bracket 632 and the second bracket 630 by joint portions 660 and 661. The joint portions 660 and 661 form pivotal joints, and joined portions are freely rotatable altogether in the x-z plane of FIG. 6 around the joint portions. The second actuator portion 391 is connected with and controlled by the control section 141 in the operation console section 140 via wiring that is not shown.

The operation of the table section 600 will now be described. Control by the control section 141 extends/contracts the first actuator portion 390 to move up/down the base plate 310. At that time, the third bracket 632 on the base plate 310 operates in exactly the same manner as the joint portion 367 shown in FIG. 4, and moves only in the vertical direction.

The second actuator portion 391 extends/contracts a distance between the second and third brackets 630 and 632 under control by the control section 141 to change the relative horizontal positions of the third bracket 632 and upper structure 320. Since the third bracket 632 moves only in the vertical direction without moving in the horizontal direction, the horizontal position of the upper structure 320 is accurately controlled by controlling the second actuator portion 391.

As described above, in Embodiment 3, the third bracket 632 disposed in the region between the joint portions 361 and 363 on the base plate 310 and the second bracket 630 secured to the upper structure 320 are connected by the second actuator portion 391; and therefore, the horizontal position of the upper structure 320 can be accurately controlled and moved while moving up/down the upper structure 320, and the carrying range when carrying the subject on the top plate 330 to the imaging region can be extended, or the driving portion 380 for carrying the top plate 330 can be reduced in size and cost by reducing functions assigned to the driving portion 380.

Many widely different embodiments of the invention may be configured without departing from the spirit and the scope of the present invention. It should be understood that the present invention is not limited to the specific embodiments described in the specification, except as defined in the appended claims.

The invention claimed is:

1. A parallel-link table comprising:
   a top plate for supporting a subject;
   an upper structure for supporting said top plate, said upper structure moving relative to said top plate only in a longitudinal direction of said top plate;
   a base plate for supporting said upper structure, said base plate moving relative to said upper structure only in said longitudinal direction;
   a platform on a floor, for supporting said top plate, said upper structure and said base plate;
   a first bracket of a height greater than a distance between said upper structure and said base plate, said first bracket being secured to said upper structure on a side near said platform;
   parallel links for coupling said base plate and said platform using a first set of movable joint portions;
   a first position correcting link of a length half that of one of said parallel links, for connecting a middle point of the one of said parallel links and said first bracket portion lying on said base plate in said longitudinal direction by a second set of movable joint portions; and
   a first actuator portion for moving said upper structure up/down with respect to said platform.

2. The parallel-link table of claim 1, wherein said upper structure has said first bracket in a portion between said parallel links.

3. The parallel-link table of claim 1, wherein said parallel links have said first set of movable joint portions on said base plate or on said platform lying at a distance greater than half the length of said first position correcting link.

4. The parallel-link table of claim 1, wherein said first actuator portion comprises a chain-belt driving portion or a roller frictional driving portion.

5. The parallel-link table of claim 1, wherein said first actuator portion comprises a cylinder having an extendable piston rod.

6. The parallel-link table of claim 1, wherein said upper structure and said base plate are connected by a linear guide.

7. The parallel-link table of claim 1, wherein said parallel links are covered with a plate material.

8. The parallel-link table of claim 1, wherein said upper structure comprises a driving portion for moving said top plate in the longitudinal direction.

9. A parallel-link table comprising:
a top plate for supporting a subject;
an upper structure for supporting said top plate, said upper structure moving relative to said top plate only in a longitudinal direction of said top plate;
a base plate for supporting said upper structure, said base plate moving relative to said upper structure only in said longitudinal direction;
a platform;
a second bracket of a height greater than a distance between said upper structure and said base plate, said second bracket being secured to said upper structure on a side near said platform, and said platform placed on a floor, for supporting said top plate, said upper structure, said base plate and said second bracket;
parallel links for coupling said base plate and said platform using movable joint portions;
a third bracket lying in a plane between said joint portions on said base plate, said third bracket being movable relative to said base plate only in said longitudinal direction;
a second position correcting link for connecting a middle point of one of said parallel links and said third bracket, said second position correcting link having a length half that of the one of said parallel links;
a second actuator portion connecting said third and second brackets; and
a first actuator portion for moving said upper structure up/down with respect to said platform.

10. The parallel-link table of claim 9, wherein said base plate and said third bracket are connected by a linear guide.

11. The parallel-link table of claim 9, wherein said parallel links have said joint portions on said base plate or on said platform lying at a distance greater than half the length of said second position correcting link.

12. The parallel-link table of claim 9, wherein said first and second actuator portions comprise a chain-belt driving portion or a roller frictional driving portion.

13. The parallel-link table of claim 9, wherein said first and second actuator portions comprise a cylinder having an extendable piston rod.

14. The parallel-link table of claim 9, wherein said upper structure and said base plate are connected by a linear guide.

15. The parallel-link table of claim 9, wherein said parallel links are covered with a plate material.

16. The parallel-link table of claim 9, wherein said upper structure comprises a driving portion for moving said top plate in the longitudinal direction.

17. A tomographic imaging apparatus comprising:
a table section for carrying a subject placed thereon to an imaging region;
an image acquisition section for acquiring tomographic image information from said subject lying in said imaging region; and
a control section for controlling the carrying of said subject to said imaging region and the acquisition of said tomographic image information, wherein
said table section comprises: a top plate for supporting said subject in a horizontally lying position; an upper structure for supporting said top plate, said upper structure moving relative to said top plate only in a longitudinal direction of said top plate; a base plate for supporting said upper structure, said base plate moving relative to said upper structure only in said longitudinal direction; a platform on a floor, for supporting said top plate, said upper structure and said base plate; a first bracket of a height greater than a distance between said upper structure and said base plate, said first bracket being secured to said upper structure on a side near said platform; parallel links for coupling said base plate and said platform using movable joint portions; a first position correcting link of a length half that of said parallel links, for connecting a middle point of one of said parallel links and said first bracket portion lying on said base plate in said longitudinal direction by movable joint portions; and a first actuator portion for moving said upper structure up/down with respect to said platform.

18. The tomographic imaging apparatus of claim 17, wherein said first actuator portion comprises a chain-belt driving portion or a roller frictional driving portion.

19. The tomographic imaging apparatus of claim 17, wherein said first actuator portion comprises a cylinder having an extendable piston rod.

* * * * *